United States Patent
Wilson et al.

(10) Patent No.: US 7,273,056 B2
(45) Date of Patent: Sep. 25, 2007

(54) OPTICAL GUIDANCE SYSTEM FOR INVASIVE CATHETER PLACEMENT

(75) Inventors: David F Wilson, Philadelphia, PA (US); Gregory J Schears, Rochester, MN (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/482,190

(22) PCT Filed: Jun. 19, 2002

(86) PCT No.: PCT/US02/19314

§ 371 (c)(1),
(2), (4) Date: Nov. 2, 2004

(87) PCT Pub. No.: WO02/103409

PCT Pub. Date: Dec. 27, 2002

(65) Prior Publication Data

US 2005/0070788 A1  Mar. 31, 2005

Related U.S. Application Data

(60) Provisional application No. 60/299,299, filed on Jun. 19, 2001.

(51) Int. Cl.
*A61B 19/00* (2006.01)

(52) U.S. Cl. .................................................... 128/899

(58) Field of Classification Search ................ 600/424, 600/473, 476; 604/510; 128/899
See application file for complete search history.

(56) References Cited

U.S. PATENT DOCUMENTS 4,096,862 A   6/1978 DeLuca ...................... 128/348

(Continued)

OTHER PUBLICATIONS

Addas, et al. *Light-guided Tracheal Puncture for Percutaneous Tracheostomy.* Canadian Journal of Anesthesia 47:919-922 (2000).

(Continued)

*Primary Examiner*—John P. Lacyk
(74) *Attorney, Agent, or Firm*—McCarter & English, LLP

(57) ABSTRACT

Light from a small laser diode is inserted in a distal end of a catheter and passed through an optical fiber that is either included in the lumen or incorporated into the wall of an invasive catheter tube during manufacture. The light is selected to be of a wavelength that is minimally absorbed by tissue, preferably in the range from about 620 nm to 1100 nm. 780 nm is preferably used as this is where the tissue absorption is near a minimum. The light passes out the end of the fiber (at the proximal end of the catheter) and through the tissue to the outside of the patient's skin where it is measured. The light pattern is observed by night vision goggles that filter out other frequencies of light. The detected light permits location of the end of the fiber, the positional accuracy depending on the thickness of tissue between the fiber tip and the exterior of the body. The method is highly accurate for small children and for catheters within a few centimeters of the skin surface of adults.

20 Claims, 3 Drawing Sheets

U.S. PATENT DOCUMENTS

| | | | | |
|---|---|---|---|---|
| 4,444,185 A | 4/1984 | Shugar | | 128/305 |
| 4,567,882 A | 2/1986 | Heller | | 128/11 |
| 4,772,093 A | 9/1988 | Abele et al. | | 350/96.25 |
| 4,782,819 A | 11/1988 | Adair | | 128/6 |
| 4,875,897 A | 10/1989 | Lee | | 604/283 |
| 4,898,175 A | 2/1990 | Noguchi | | 128/634 |
| 4,945,895 A | 8/1990 | Takai et al. | | 128/6 |
| 5,005,180 A | 4/1991 | Edelman et al. | | 372/57 |
| 5,005,573 A | 4/1991 | Buchanan | | 128/207 |
| 5,005,592 A | 4/1991 | Cartmell | | |
| 5,007,408 A | 4/1991 | Ieoka | | 128/6 |
| 5,019,040 A | 5/1991 | Itaoka et al. | | 604/95 |
| 5,125,404 A | 6/1992 | Kittrell et al. | | 128/634 |
| 5,131,380 A | 7/1992 | Heller et al. | | 128/6 |
| 5,196,004 A | 3/1993 | Sinofsky | | 606/3 |
| 5,197,470 A | 3/1993 | Helfer et al. | | 128/634 |
| 5,263,928 A | 11/1993 | Trauthen et al. | | 604/53 |
| 5,268,570 A * | 12/1993 | Kim | | 250/214 VT |
| 5,290,275 A | 3/1994 | Kittrell et al. | | 606/15 |
| 5,370,640 A | 12/1994 | Kolff | | 606/2 |
| 5,415,654 A | 5/1995 | Daikuzono | | 606/15 |
| 5,423,311 A | 6/1995 | Snoke et al. | | 128/6 |
| 5,423,321 A | 6/1995 | Fontenot | | 128/664 |
| 5,448,582 A | 9/1995 | Lawandy | | 372/42 |
| 5,453,086 A | 9/1995 | Weber | | 604/20 |
| 5,456,680 A | 10/1995 | Taylor et al. | | 606/2 |
| 5,496,305 A | 3/1996 | Kittrell et al. | | 606/15 |
| 5,514,128 A | 5/1996 | Hillsman et al. | | 606/7 |
| 5,517,997 A | 5/1996 | Fontenot | | 128/664 |
| 5,540,691 A | 7/1996 | Elstrom et al. | | 606/64 |
| 5,643,251 A | 7/1997 | Hillsman et al. | | 606/7 |
| 5,665,052 A | 9/1997 | Bullard | | 600/194 |
| 5,728,092 A | 3/1998 | Doiron et al. | | 606/15 |
| 5,733,277 A | 3/1998 | Pallarito | | 606/7 |
| 5,879,306 A | 3/1999 | Fontenot et al. | | 600/473 |
| 5,906,579 A | 5/1999 | Vander Salm et al. | | 600/424 |
| 5,947,958 A | 9/1999 | Woodard et al. | | 606/15 |
| 5,995,208 A | 11/1999 | Sarge et al. | | 356/39 |
| 6,048,349 A | 4/2000 | Winston et al. | | 606/108 |
| 6,061,587 A | 5/2000 | Kucharczyk et al. | | 600/411 |
| 6,063,093 A | 5/2000 | Winston et al. | | 606/108 |
| 6,081,741 A | 6/2000 | Hollis | | 600/424 |
| 6,113,588 A | 9/2000 | Duhaylongsod et al. | | 606/15 |
| 6,134,003 A | 10/2000 | Tearney et al. | | 356/345 |
| 6,146,409 A | 11/2000 | Overholt et al. | | 607/88 |
| 6,159,203 A | 12/2000 | Sinofsky | | 606/7 |
| 6,230,046 B1 | 5/2001 | Crane et al. | | 600/476 |
| 6,236,879 B1 | 5/2001 | Konings | | |
| 6,246,901 B1 | 6/2001 | Benaron | | 600/431 |
| 6,332,089 B1 | 12/2001 | Acker et al. | | |
| 6,366,726 B1 | 4/2002 | Wach et al. | | 385/115 |
| 6,445,943 B1 | 9/2002 | Ferre et al. | | 600/424 |
| 6,463,313 B1 | 10/2002 | Winston et al. | | 600/407 |
| 6,475,226 B1 | 11/2002 | Belef et al. | | 606/185 |
| 6,519,485 B2 | 2/2003 | Wiesmann et al. | | 600/328 |
| 6,572,609 B1 | 6/2003 | Farr et al. | | |
| 6,685,666 B1 | 2/2004 | Fontenot | | 604/27 |
| 6,811,544 B2 | 11/2004 | Schaer | | 604/95.04 |
| 6,852,109 B2 | 2/2005 | Winston et al. | | 606/41 |
| 6,887,229 B1 | 5/2005 | Kurth | | 604/525 |
| 6,902,545 B2 | 6/2005 | Bertolero et al. | | 604/102.03 |
| 2002/0038120 A1 | 3/2002 | Duhaylongsod et al. | | 606/15 |
| 2002/0052597 A1 | 5/2002 | Duhaylongsod et al. | | 606/15 |
| 2002/0115922 A1 | 8/2002 | Waner et al. | | 600/407 |
| 2002/0123696 A1 | 9/2002 | Kokate et al. | | |
| 2002/0161290 A1 | 10/2002 | Chance | | 600/323 |
| 2003/0092995 A1 | 5/2003 | Thompson | | 600/473 |
| 2003/0130575 A1 | 7/2003 | Desai | | 600/417 |
| 2003/0187360 A1 | 10/2003 | Waner et al. | | 600/478 |
| 2003/0191379 A1 | 10/2003 | Benaron et al. | | 600/323 |
| 2003/0191398 A1 | 10/2003 | Motz et al. | | 600/478 |
| 2004/0019280 A1 | 1/2004 | Waner et al. | | 600/466 |
| 2004/0064021 A1 | 4/2004 | Pfeiffer | | 600/341 |
| 2004/0064022 A1 | 4/2004 | Korn | | 600/342 |
| 2004/0068178 A1 | 4/2004 | Govari | | |
| 2004/0073120 A1 | 4/2004 | Motz et al. | | 600/478 |
| 2004/0093044 A1 | 5/2004 | Rychnovsky et al. | | |
| 2004/0236231 A1 | 11/2004 | Knighton et al. | | 600/476 |
| 2005/0165462 A1 | 7/2005 | Bays et al. | | 607/88 |
| 2005/0240147 A1 | 10/2005 | Makower et al. | | 604/96.01 |

OTHER PUBLICATIONS

Heller et al. *Early Experience with Illuminated Endotracheal Tubes in Premature and Term Infants*. The American Academy of Pediatrics, vol. 75, Issue 4, pp. 664-666. Apr. 1, 1985.

The Laerdal Foundation. *Trachlight® Stylet and Tracheal Lightwand*; www.laerdal.com.au/document.asp?subnodeid-8619239. Jun. 4, 2005.

University of Virginia Health System. *Airway Management—How to Intubate*. www.healthsystems.virginia.edu/Internet/Anesthesiology-Elective/airway/Intubation.cfm. Jun. 4, 2005.

Weiss, Markus. *Video-Assisted Airway Management*. The Internet Journal of Anesthesiology. 1999. vol. 3, No. 1.

Zanardo V. et al. *Correct Placement of Endotracheal Tube by Single Strand Fiberoptic Light in Prematures.* (*Initial Clinical Experience*). Padiatr Padol. 1991:26(5):227-8.

PCT International Search Report dated May 9, 2006.

* cited by examiner

OPTICAL GUIDANCE SYSTEM FOR INVASIVE CATHETER PLACEMENT

CROSS-REFERENCE TO RELATED APPLICATIONS

This application is the National Stage of International Application No. PCT/US02/19314, filed Jun. 19, 2002, which claims the benefit of U.S. Provisional Application Nos. 60/299,299, filed Jun. 19, 2001.

FIELD OF THE INVENTION

The present invention relates to an optical guidance system and a method for insertion of endotracheal tubing, nasogastric tubing, feeding tubing, epidural catheters, central venous catheters, peripherally inserted central venous catheters, chest tubes, pleural catheters, and similar invasive catheters and tubes.

DESCRIPTION OF THE PRIOR ART

Determining the location of the end of a catheter inserted into patients for the purpose of providing nutrients or medications to specific locations within the body has been difficult. Currently, catheter placement is either done without visual guidance or, if the placement is particularly critical, it is done by x-ray, which can accurately determine the location of radio-opaque plastic materials used in making the tubing. However, multiple x-rays are often necessary. The necessity for multiple x-rays in order to locate the end of the inserted tubing is undesirable. An optical system that is convenient and easy to use and yet allows the end of the tubing to be quite accurately located without the use of x-rays is desired. Preferably, the position of the catheter tip may be directly observed during the insertion process and the position of the tip checked at any time thereafter.

Prior art catheter light delivery devices are known (e.g., Woodward et al; U.S. Pat. No. 5,947,958) that provide illumination of internal organs of a patient after insertion through, for example, the peritoneal wall. This illumination is to provide light for either imaging of the tissue surface or for delivering the light used in photodynamic therapy. Such devices are not used for catheter placement.

Other light guides, such as Fontenot; U.S. Pat. No. 5,423,321, have multiple light guiding fibers of different lengths that are inserted into internal organs or vessels during surgery. In the case of balloon catheters, such light guides are used to place the balloon catheter in positions where inflation of the balloon will occlude the vessel if that should become necessary. The light guide is an independent entity and observation is through the vessel wall such that visible light is sufficient, although near infra red light is indicated as decreasing the intensity of light that is required. A detection system is also described for determining when the surgical cutting tool approaches the vessel.

Vander Salm et al; U.S. Pat. No. 5,906,579 and Duhaylongsod et al; U.S. Pat. No. 6,113,588 similarly describe methods for visualizing balloon catheters through the vessel wall under surgical conditions. In these devices, the optical fiber is an independent entity and is preferably inserted through one lumen of a multilumen catheter. The disclosed devices are specifically disclosed for use in cardiothoracic surgery.

Such prior art light guides do not use a single fiber that is built into the structure of catheters with multiple different functions, are not directed primarily to localizing the tip of an inserted catheter during non-surgical procedures for endotracheal tubing, nasogastric tubing, feeding tubing, epidural catheterization, central venous catheterization, peripherally inserted central venous catheterizations, chest tubes pleural catheterization, or with similar invasive catheters and tubes, and such prior art devices do not use only near infrared light since the vessels are not surgically exposed and visible light (blue through orange) provides insufficient penetration of the tissue. Moreover, such prior art devices are relatively expensive and the optical components may require difficult FDA scrutiny since they may contact the patient. The present invention addresses these limitations in the prior art.

SUMMARY OF THE INVENTION

Light from a small laser diode is passed through an optical fiber that is either included in the lumen or incorporated into the wall of an invasive catheter tube during manufacture. The light is selected to be of a wavelength that is minimally absorbed by tissue, preferably in the range from about 620 nm to 1100 nm. In a preferred embodiment, 780 nm is used as this is where the tissue absorption is near a minimum. The light passes out the end of the fiber (at the distal end of the catheter) and through the tissue to the outside where it is measured. The light pattern is observed by night vision goggles that filter out light in other frequency ranges. The detected light allows location of the end of the fiber, the positional accuracy depending on the thickness of tissue between the fiber tip and the exterior of the body. The method is highly accurate for small children and for catheters near the skin surface of adults but may not be applicable to catheters placed within the body cavity of some large adults.

BRIEF DESCRIPTION OF THE DRAWINGS

An optical guidance system and method for insertion of endotracheal tubing, nasogastric tubing, feeding tubing, epidural catheters, central venous catheters, peripherally inserted central venous catheters, chest tubes pleural catheters, and similar invasive catheters and tubes in accordance with the invention is further described below with reference to the accompanying drawings.

DETAILED DESCRIPTION OF THE INVENTION

Figure 1:
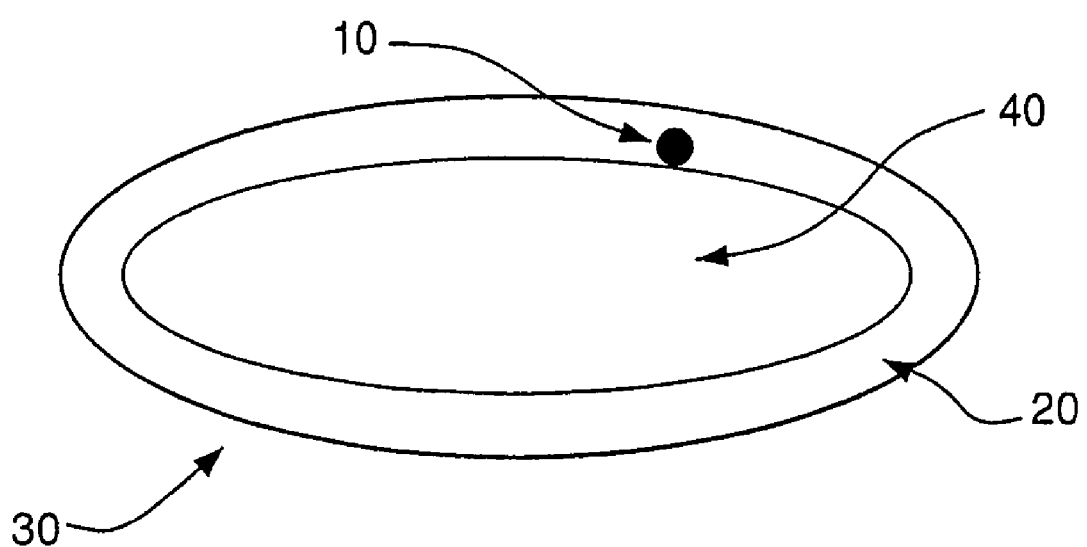
FIG. 1 illustrates a cross-section of a catheter with an integral optical fiber that is used in accordance with the invention to locate the tip of the inserted catheter.
Figure 2:
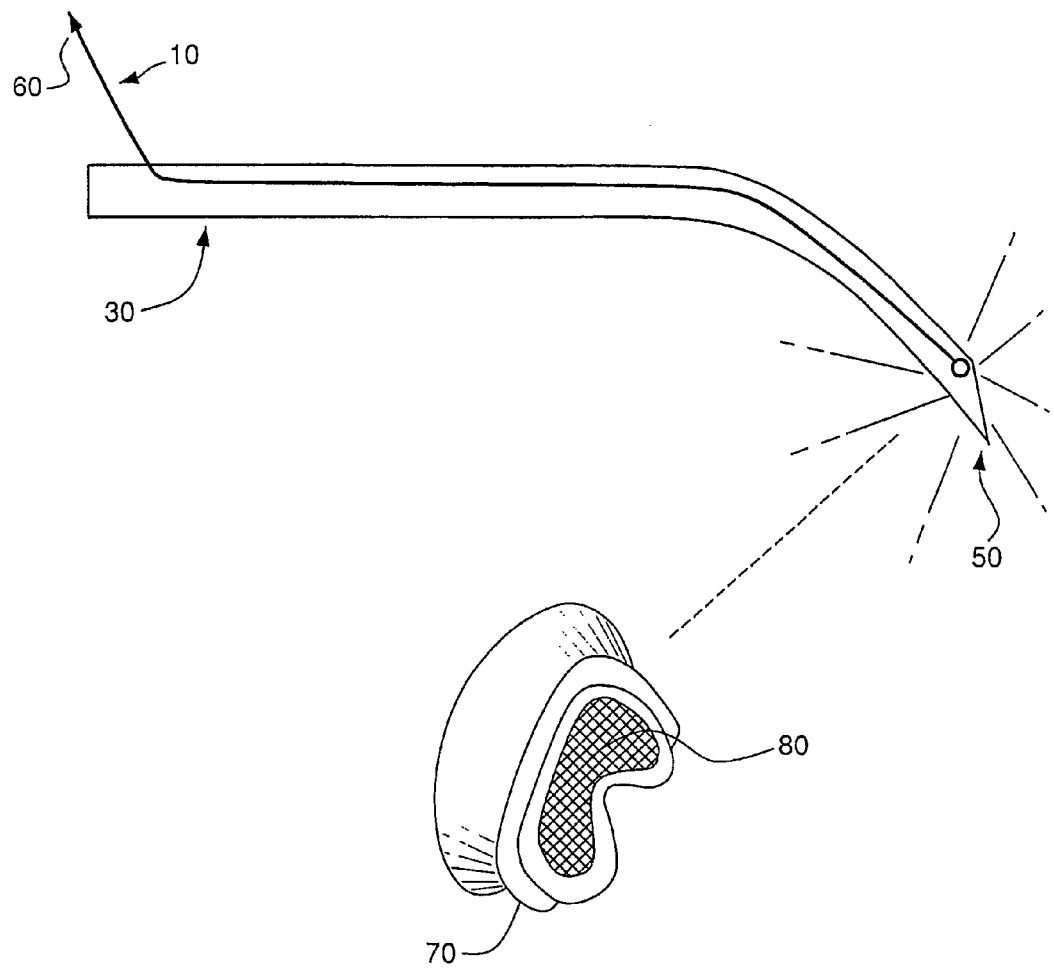
FIG. 2 illustrates a side view of the catheter of FIG. 1.

An optical guidance system in accordance with the invention includes a laser diode having a wavelength in the range of 620 nm to 1100 nm, preferably a 780 nm wavelength with an emission less than 2 nm wide and less than 5 mW in power that/is carried through a 150 micron (or less) core glass optical fiber to an "ST" optical connector at a distal end. As shown in FIG. 1, the glass optical fiber 10 is embedded in (i.e., partially or completely surrounded by) the wall 20 of a catheter 30 having a catheter lumen 40. The optical fiber 10 runs the entire length of the catheter 30, and the unterminated end of the optical fiber 10 at the distal end 50 of the catheter 30 is adapted to be inserted into the patient as shown in FIG. 2. The proximal end 60 is terminated with an ST optical connector (not shown) appropriate for connecting the optical fiber 10 with the laser diode (not shown) Conversely, the optical fiber 10 may be inserted into lumen 40 of the catheter 30 at its proximal end 60 and fed to the distal tip 50 of the catheter 30 and held in place so that light escapes from the distal end 50 once the catheter 30 is inserted into the patient.

The operator uses a detection system such as near infrared "night vision" goggles 70 watch the progress of the catheter 30 from the site of entry to the chosen location. The distal end 50 of the catheter 30 is treated as a single light source and the diffuse rays from this light source are detected. A narrow pass (<10 nm at half height is preferred, although wider bandpass filters could be used) interference filter 80 with a center wavelength of 780 nm (for a light source of 780 nm) is used to cover the detector surface of the goggles 70. In general, contribution of other ambient lighting increases with increasing width of the optical filter bandpass. The value of less than 10 nm is selected to allow some variation in the laser diode wavelength and yet to minimize the amount of light other than that from the laser diode that passes through to the detector of the goggles 70. Of course, if other wavelength light were used, an appropriate interference filter centered about the other wavelength would be used.

Figure 3:
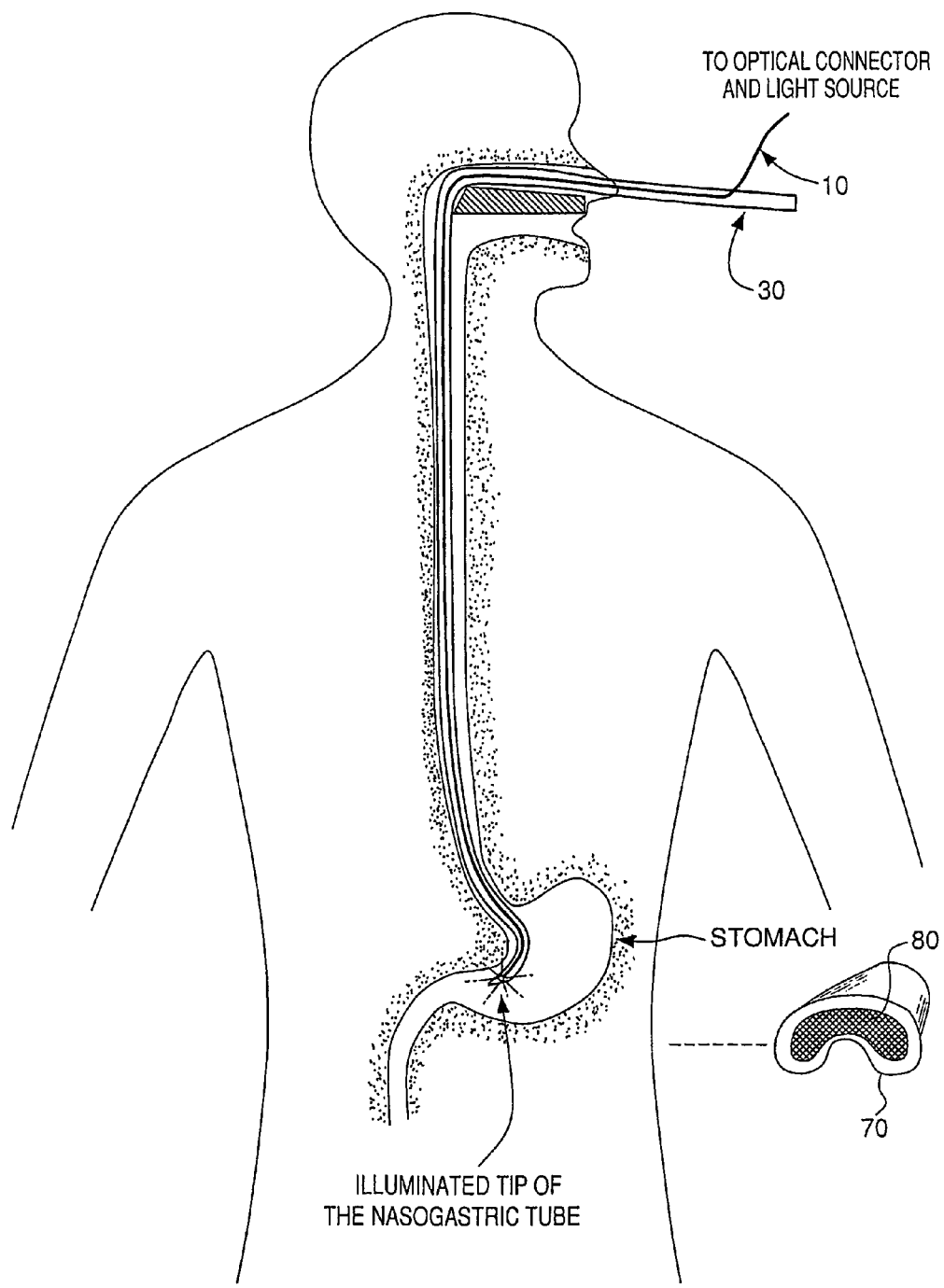
FIG. 3 illustrates the catheter of FIG. 1 inserted into the body of a patient and the detection of the light from the tip of the catheter at the nearest spot of the patient's skin in accordance with the method of the invention.

FIG. 3 illustrates the catheter 30 of FIGS. 1 and 2 inserted into the body of a patient vie a nasogastric catheter 30 and the detection of the light from the tip 50 of the catheter 30 at the nearest spot of the patient's skin in accordance with the method of the invention. In the example illustrated in FIG. 3, night vision goggles 70 with an appropriate interference filter 80 thereon allow the operator to see the infrared light through the skin outside of the patient's stomach.

Those skilled in the art will appreciate that other designs of the optical guidance system for catheters in accordance with the invention could be constructed using different light sources and light detectors. While 780 nm light is suitable since tissue absorption is near a minimum at that wavelength, it would be possible, for example, to use an LED as a light source as long as the light provided was of appropriate wavelength and energy. In this case, a wider bandpass filter may be required on the detector (an LED light output is broader than that of the laser diode). Similarly, different detectors could be used, including photodiodes, photomultipliers, avalanche photodiodes, and microchannel plates. When photodiodes or other single site detectors are used they could be moved over the surface of the tissue to detect the maximum in the specific light emitted from the optical fiber. The sensitivity of the measurement could be maximized by modulating the light at a specific frequency (such as 1000 Hz) and detecting only the photosignal of that frequency.

Another modification that would allow the operator to detect those cases in which the catheter had "doubled back" inappropriately would be to incorporate two optical fibers, one terminated about 5 centimeters before the tip and the other at the tip. The two could be distinguished by differences in modulation frequency and/or wavelengths of light.

In one variation of the detection system, the night vision goggle 70 could include a sensitive microchannel plate imager in a mini-display directly in front of one eye of the operator. This would allow the operator to look at either the patient or at the display as desired.

Although exemplary implementations of the invention have been described in detail above, those skilled in the art will readily appreciate that many additional modifications are possible in the exemplary embodiments without materially departing from the novel teachings and advantages of the invention. Any such modifications are intended to be included within the scope of this invention as defined by the following exemplary claims.

We claim:

1. An optical guidance system for directing the placement of an optically-guided catheter within a body cavity or lumen of a patient, the system comprising:
    an optically-guided catheter having a proximal end, a distal end, and a lumen;
    an optical fiber component of the catheter and extending to a distal end of the catheter;
    a light-emitting region at the distal end of the optical fiber component of the catheter, wherein light is provided to the light-emitting region from a light source when the catheter is placed within the body cavity or lumen of the patient, and the emitted light passes through the patient's tissue to the outside of the patient's body; and
    an external detection device further comprising a filter to block light in wavelength ranges outside of a range of wavelengths of light emitted by the light source, whereby light emitted to the outside of the patient's body from the light-emitting region is detected to assist an operator in determining the location of the distal end of the catheter within the patient's body, thereby indicating the distal end of the catheter within the body cavity or lumen of the patient.

2. The optical guidance system as in claim 1, wherein the light source comprises one of an LED and a laser diode that emits light in a wavelength range of 620 nm to 1100 nm.

3. The optical guidance system as in claim 2, wherein the light source emits light at a wavelength of approximately 780 nm.

4. The optical guidance system as in claim 1, further comprising a detection device that receives the light emitted outside of the patient's body from the light emitting region.

5. An optical guidance system as in claim 4, wherein said detection device comprises a night vision light detector having an interference filter over a detection surface thereof, the interference filter effectively blocking light in wavelength ranges outside of a narrow band including a wavelength range emitted by the light source.

6. The optical guidance system as in claim 5, wherein the night vision detection light detector comprises a microchannel plate imager in a mini-display directly in front of one eye of the operator of the system.

7. The optical guidance system as in claim 4, wherein the detection device comprises at least one photodiode, photomultiplier, avalanche photodiode, or microchannel plate, or combination thereof.

8. The optical guidance system as in claim 1, wherein the optical fiber is embedded in a wall of the catheter.

9. The optical guidance system as in claim 1, wherein the optical fiber is inserted into a lumen of the catheter so as to extend to the distal end of the catheter and the optical fiber is held in place therein or thereon.

10. A method of determining the location of a distal end of an optically-guided catheter inserted into a body cavity or lumen of a patient, the method comprising the steps of:
    inserting the optically-guided catheter into the body cavity or lumen of the patient, wherein an optical fiber extends to the distal end of the catheter;

providing light into the optical fiber in the catheter, whereby the emitted light passes through the optical fiber to the distal end of the catheter when the catheter is inserted in the body cavity or lumen of the patient;

emitting light from a light-emitting region at the distal end of the optical fiber in the catheter, whereby the emitted light passes through the patient's tissue to the outside of the patient's body;

externally detecting light emitted from the light-emitting region on the catheter within the patient after it passes through a filter to block light in wavelength ranges outside of a range of wavelengths of light emitted by the light source; and determining location of the light-emitting region at the distal end of the catheter from the light detected at the surface of the patient's skin, thereby determining placement of the catheter within the body cavity or lumen of the patient, based upon the location of the light-emitting region.

11. The method as in claim 10, wherein the light inserting step comprises the step of inserting light in a wavelength range of 620 nm to 1100 nm into the optical fiber.

12. The method as in claim 11, wherein the light inserting step comprises the step of inserting light at a wavelength of approximately 780 nm into the optical fiber.

13. The method as in claim 10, wherein the detecting step further comprises viewing the patient's body with a night vision light detector having an interference filter on its detection surface.

14. The method as in claim 13, wherein the light inserted into the optical fiber is narrowband light and the determining step includes the step of filtering emitted light through the interference filter so as to effectively block light in wavelength ranges outside of a wavelength range of the narrowband light inserted into the optical fiber.

15. The method of claim 13, wherein the detecting step further comprises the step of providing a mini-display in front of one eye of an operator using a night vision light detector.

16. The method as in claim 10, wherein the detecting step comprises the step of detecting light emitted from the optically guided catheter using at least one photodiode, photomultiplier, avalanche photodiode, and microchannel plate, or combination thereof.

17. The method as in claim 10, wherein the optical fiber is embedded into a wall of the catheter.

18. The method as in claim 10, wherein the optical fiber is inserted into a lumen of the catheter so as to extend to the distal end of the catheter and holding the optical fiber in place therein.

19. An optical guidance system for directing the placement of an invasive catheter within a patient, comprising:

a catheter tube;

an optical fiber inserted into said catheter tube so as to extend to a distal end of said catheter tube;

a light source arranged to insert light into said optical fiber whereby the inserted light passes through the optical fiber to the distal end of the catheter when the catheter is inserted in a patient, and the light emitted from the distal end of the inserted catheter passes through the patient's tissue to the outside of the patient's body; and a second optical fiber inserted into said catheter tube and terminating at a terminating position a predetermined distance proximal to a terminating position of said optical fiber and carrying light having at least one of (1) a difference in modulation frequency with light carried by said optical fiber and (2) a difference in wavelength with light carried by said optical fiber, whereby doubling back of said catheter tube during insertion may be determined from positions of the light emitted from the respective optical fibers through the patient's tissue to the outside of the patient's body;

whereby the light emitted outside of the patient's body is detected to assist an operator in determining the location of the distal end of the catheter within the patient's body.

20. A method of determining the location of a distal end of an invasive catheter inserted into a patient, comprising the steps of:

inserting into a patient an invasive catheter having an optical fiber inserted therein so as to extend to a distal end of the catheter;

inserting light into the optical fiber, whereby the inserted light passes through the optical fiber to the distal end of the catheter when the catheter is inserted in a patient, and the light emitted from the distal end of the inserted catheter passes through the patient's tissue to the outside of the patient's body;

inserting a second optical fiber into the catheter so that said second optical fiber terminates a predetermined distance short of said distal end of said catheter;

inserting light into said second optical fiber that can be distinguished from light inserted into said optical fiber;

detecting light emitted through the patient's skin from respective ends of each optical fiber;

determining the location of the distal end of the catheter from the light detected at the surface of the patient's skin; and determining whether the catheter has "doubled back" on itself during insertion based on the detected locations of light emitted through the patient's skin.

* * * * *